United States Patent [19]

Armeniades et al.

[11] Patent Number: 4,548,205
[45] Date of Patent: Oct. 22, 1985

[54] OPHTHALMIC INSTRUMENT FOR MEASURING INTRAOCULAR FLUID PRESSURE

[76] Inventors: C. D. Armeniades, 2127 Addison Rd., Houston, Tex. 77030; Louise C. Moorhead, 3803 University Blvd., Houston, Tex. 77005

[21] Appl. No.: 436,953

[22] Filed: Oct. 27, 1982

[51] Int. Cl.[4] .............................................. A61B 5/02
[52] U.S. Cl. ..................................... 128/748; 128/675
[58] Field of Search ............... 128/673, 675, 676, 748, 128/645; 73/721, 66, 727

[56] References Cited

U.S. PATENT DOCUMENTS

| | | | |
|---|---|---|---|
| 3,088,323 | 5/1963 | Welkowitz | 128/675 X |
| 3,550,583 | 12/1970 | Chiku et al. | 73/727 X |
| 3,553,625 | 1/1971 | Stedman | 128/748 X |
| 3,710,781 | 1/1973 | Huthcins, IV et al. | 128/675 |
| 3,939,823 | 2/1976 | Kaye et al. | 128/748 |
| 4,274,423 | 6/1981 | Mizuno et al. | 128/675 |

OTHER PUBLICATIONS

Matsumoto, H. et al., "The Development of a Fibre Optic Catheter Tip Pressure Transducer", *J. Med. Engr. & Tech*, vol. 2, No. 5, (Sep. 1978), pp. 239–242.

*Primary Examiner*—Edward M. Coven
*Attorney, Agent, or Firm*—Pravel, Gambrell, Hewitt & Kimball

[57] ABSTRACT

An ophthalmic device and system for measuring relative pressure of fluid inside an ocular globe includes an elongated surgical instrument which is adapted to penetrate the ocular globe. A fluid pressure transducer is mounted on the instrument in a position to communicate with fluid inside the ocular globe and generate signals in response to pressure changes in the fluid. The signal is transmitted external of the instrument to a pump or other fluid transfer device which is operatively connected to the transducer for receiving the signals and supplying or removing fluid from the ocular globe in response to predetermined signals. A conduit is operatively connected to the fluid transfer device and adapted to communicate with the interior of the ocular globe through which fluid can flow between the fluid transfer device and the ocular globe.

18 Claims, 6 Drawing Figures

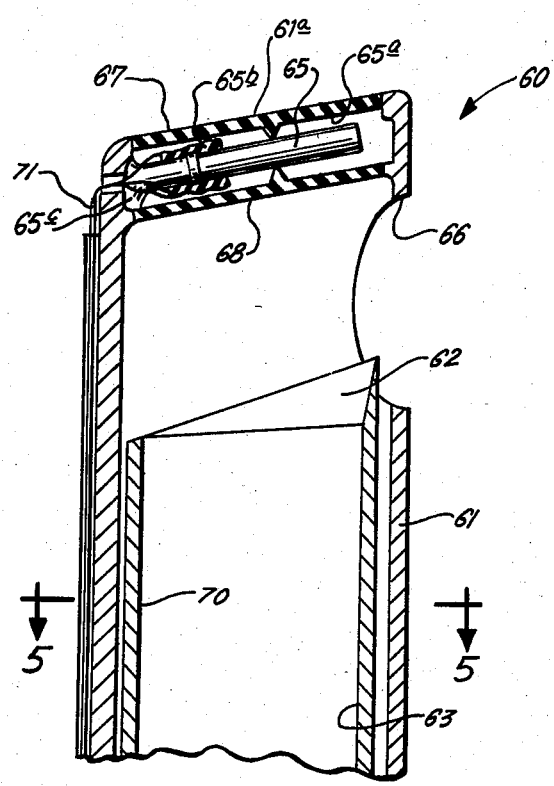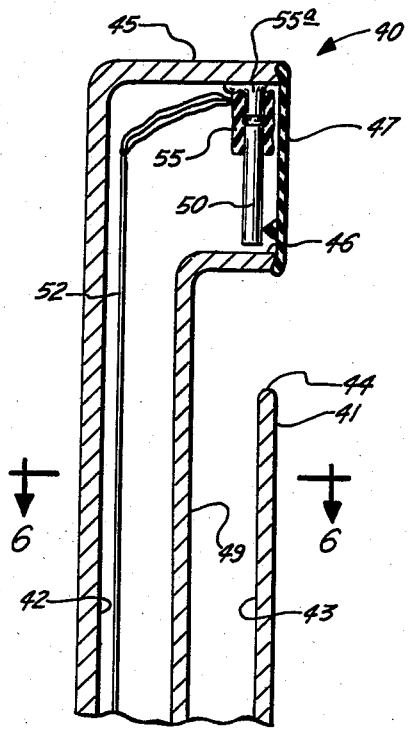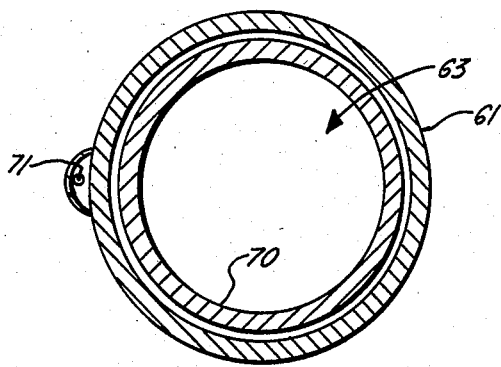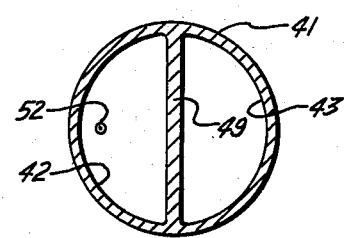

OPHTHALMIC INSTRUMENT FOR MEASURING INTRAOCULAR FLUID PRESSURE

BACKGROUND OF THE INVENTION

1. Field of Invention

The present invention relates to ophthalmic microsurgical instruments and, more particularly, to such surgical instrumentation which continuously monitors internal ocular globe fluid pressure during ophthalmic surgical procedures and the like.

2. General Background

A large number of microsurgical procedures inside the eye are performed through "closed systems" which maintain the integrity and internal pressure of the ocular globe while microsurgical instruments are used to penetrate the eye through one or more small incisions (see FIG. 1).

Exemplary functions performed by these instruments are:

Fragmentation—the cutting and separation of ocular tissue, such as the lens in cataract surgery or fibrous and membrane-like growths inside the vitreous (e.g., vitrectomy, membranectomy);

Emulsification—the mechanical digestion of tissue (usually the lens) by means of ultrasound in order to facilitate its removal through small incisions;

Irrigation (infusion)—the introduction of a saline solution into the operating field by means of gravity or positive pressure; and Aspiration (suction)—the removal of fluid and/or entrained tissue fragments by means of vacuum.

The surgeon combines irrigation and aspiration to transport tissue fragments away from the operating field. He or she also uses these functions to maintain intraocular pressure during the surgical procedure. Control of pressure in irrigation and aspiration is extremely important. If the aspiration suction is too strong (due to excessive vacuum) it may damage endothelial cells during anterior chamber surgery or may cause retinal detachment in vitrectomy procedures. Too high an irrigation pressure or excessive variations in the pressure or flow rate of the irrigation fluid may traumatize ocular tissue.

With traditional instrumentation the level of irrigation flow and range of aspiration vacuum are adjusted by a surgical assistant in response to the surgeon's instruction. Available systems afford the surgeon direct control of these variables, usually by means of fingertip or footpedal switches, and provide visual or audio indications of aspiration pressure (vacuum) and irrigation flow. See, for example, U.S. Pat. No. 4,168,707 entitled "Control Apparatus for Microsurgical Instruments."

Generally, such pressure sensors are located in a remote instrument console located a distance of 1-2 meters from the operating site and connected to it through thin, flexible plastic tubing containing a saline solution. Such remote monitoring of pressure has the potential of introducing significant errors in pressure measurements due to the compliance of the tubing and the inertia and viscosity of the fluid column interposed between the surgical site and pressure sensor location. Such errors become more pronounced when air bubbles and tissue fragments enter the flexible conduit which transmits fluid between the operative site and instrument console.

Since a surgeon must depend primarily on visual observation and feel of the surgical site to guide him in controlling the level of suction and irrigation flow rate, knowledge of the accurate pressure or vacuum forces exerted on the tissue at the operating site would enhance greatly the ease and safety of the procedure. Furthermore, accurate control of intraocular pressure both during intraocular surgery and at the time of final wound closure would help minimize postoperative overpressure and associated dangers to the patient.

While there are many devices which are associated with ophthalmic surgical procedures, none is known which accurately monitors internal ocular pressure during surgery. For example, Russian Pat. No. 733,670 teaches the use of a strain gauge in the cutting tip of an ophthalmic surgical instrument and a variable audible signal is generated in response to tissue pressure encountered by the instrument when cutting, but internal pressure is not measured.

U.S. Pat. No. 3,945,375 is directed to an ophthalmic surgical instrument for removing tissue and includes a rotating fluted cutter housed in a probe adapted to be inserted into a portion of the body from which tissue is to be removed. The instrument can supply irrigation fluid through the probe to the area being operated upon and evacuate the material through the probe after being engaged by the cutter, but does not monitor internal pressure.

U.S. Pat. No. 4,117,843 teaches a system which controls the infusion of fluid to a closed operating field such as an eye at a selected predetermined pressure in addition to being able to sever material in the field and for evacuating the severed material in a suspension or emulsion of the infusion fluid. However, internal pressure is not measured.

U.S. Pat. No. 4,168,707 relates to an electronic control for microsurgical instruments which is adapted for use in intraocular surgery. Commands received from a surgeon's foot control unit control the various aspiration functions normally performed manually by a surgical assistant. A typical control system used to perform the infusion and aspiration functions required during intraocular survery is described in detail.

There are also various patents which deal with strain gauges that are used to measure blood pressure. See, for example, U.S. Pat. Nos. 2,959,056; 3,550,583; 3,946,724; and 4,274,423. Blood pressure transducers implantable in arteries or veins are described in U.S. Pat. Nos. 3,724,274 and 3,748,623. U.S. Pat. Nos. 4,274,423 teaches a catheter for use in determining pressures within blood vessels and the heart. And U.S. Pat. No. 4,175,566 is directed to a fluid velocity flow probe.

U.S. Pat. No. 3,776,238 relates to an instrument with two tubes that are mounted co-axially within one another with an opening adjacent the end of the outer tube. Cutting of the vitreous and fibrous bands in the eye caused by hemorrhaging is performed by a chopping action of the sharp end of the inner tube against the inner surface of the end of the outer tube and the bands are removed by suction through the inner tube. The removed vitreous is continuously replaced by a saline solution introduced into the eye through the instrument.

None of these prior art devices provides an ophthalmic microsurgical instrument which can monitor internal fluid pressure during ophthalmic surgery.

SUMMARY OF THE PRESENT INVENTION

The subject invention is directed to an apparatus for measuring in-situ fluid pressure of the ocular globe during ophthalmic surgery so that internal pressure can be accurately controlled.

The apparatus of the present invention senses the intraocular pressure exerted on the tip of the microsurgical instrument or local suction forces on tissue removed through aspiration. An electric signal generated in response to relative pressure changes can be used to regulate automatically aspiration vacuum level or irrigation flow rate within acceptable ranges for providing an extra measure of safety to those surgical procedures.

The instrument includes an elongated needle-like instrument with a pressure transducer mounted in its tip in communication with the intraocular fluid after the instrument has entered the ocular globe. The transducer is capable of measuring either the static pressure of ocular fluid surrounding the instrument relative to ambient atmospheric pressure or local suction forces in the instrument opening exerted on diseased tissue as the tissue is aspirated.

The ocular instrument utilizes a miniature pressure sensor located behind a thin, flexible diaphragm at a small opening near the tip of the instrument. The diaphragm can be constructed from natural rubber or other suitable elastomer and serves as a barrier between the channel containing the pressure sensor and the external environment. The diaphragm is connected to the transducer and operates to transmit forces to the transducer as a result of pressure differences between these two environments causing the diaphragm to move.

The transducer is a suitable, miniaturized pressure transducer with appropriate sensitivity and stability. An electric signal is generated by the transducer, which is transmitted to an instrument console where it is amplified and displayed. The signal can be used to activate known feedback control circuits to operate a valve for regulating or limiting suction vacuum or irrigation fluid flow through the same or another instrument.

Accordingly, it is an object of this invention to provide an ophthalmic surgical instrument which accurately and safely measures the pressure exerted by ocular fluids or tissues at the site of microsurgical activity.

Another object of the invention is to provide an accurate pressure valve signal to feedback control circuits which automatically regulates and/or limits suction vacuum or regulates the flow and pressure of the irrigation fluid responsive to sensed intraocular pressure.

The instrument which is the subject of the present invention provides a number of controls during anterior chamber or cataract surgery such as, for example: (1) control of anterior chamber depth (space between cornea and iris); (2) better regulation of bleeding by precise pressure tamponade; (3) accurate measurement of intraocular pressure through a second site during wound closure; (4) better control of suture tension during wound closure to avoid astigmatism; and (5) better approximation of physiologic intraocular pressure after wound closure.

Controls afforded by the invention during vitreous surgery include: (1) measurement and control of aspiration forces applied to diseased tissue at the instant of excision and limitation of these forces to avoid retinal detachment; (2) regulation of vitreous pressure from a second site in order to control bleeding during surgery; and (3) better approximation of physiologic intraocular pressure after wound closure.

BRIEF DESCRIPTION OF THE DRAWINGS

For a better understanding of the nature and objects of the present invention, reference should be had to the following detailed description, taken in conjunction with the accompanying drawings, in which:

FIG. 3 is a sectional view of one embodiment of the invention where a pressure transducer is mounted to provide communication between the interior of the ocular globe and an internal conduit of an instrument of the type shown in FIG. 2;

FIG. 4 is another embodiment of the invention in which the transducer communicates directly with the interior of the ocular globe;

FIG. 5 is a sectional view looking along lines 5—5 of FIG. 3; and

FIG. 6 is a sectional view looking along lines 6—6 of FIG. 4.

DETAILED DESCRIPTION OF PREFERRED EMBODIMENTS

Figure 1:
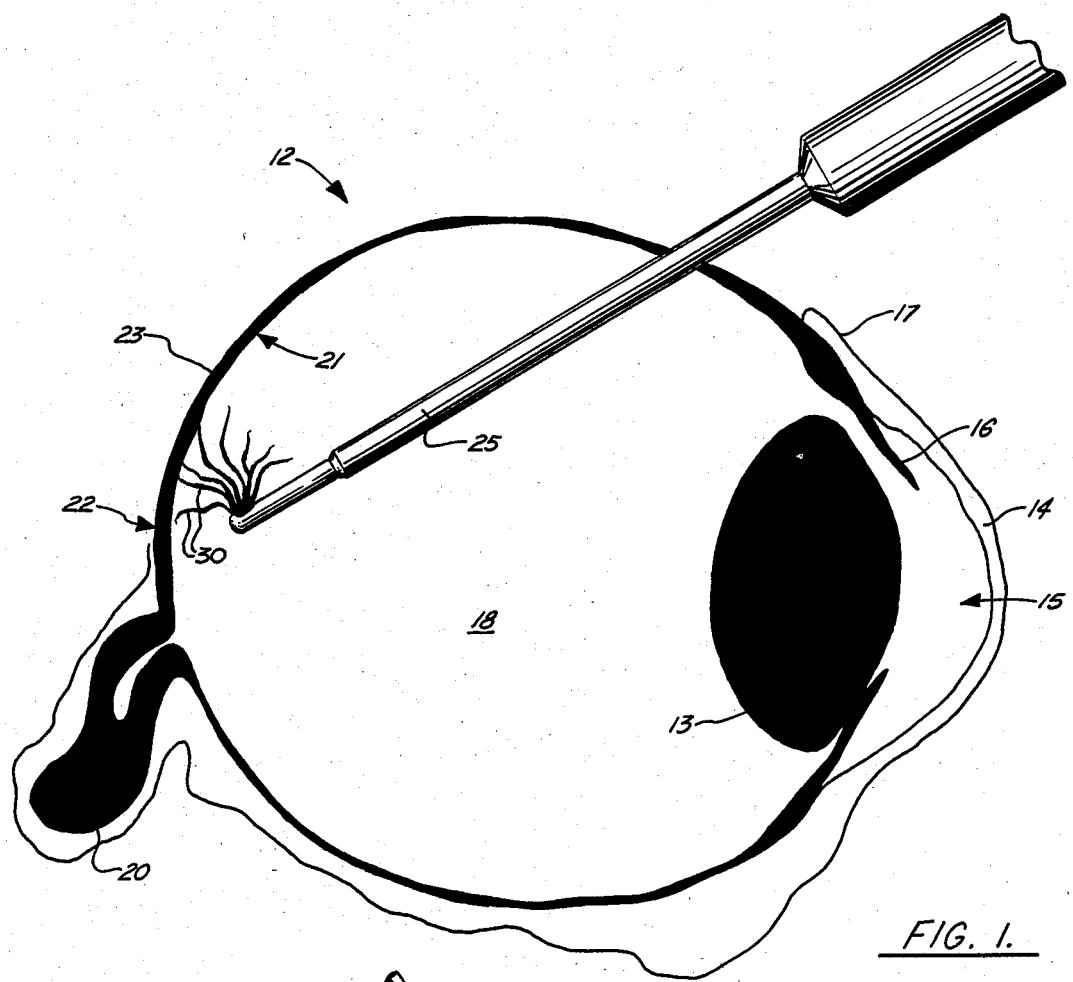
FIG. 1 is a schematic section view illustrating a "closed system" surgical procedure in the eye.
Figure 2:
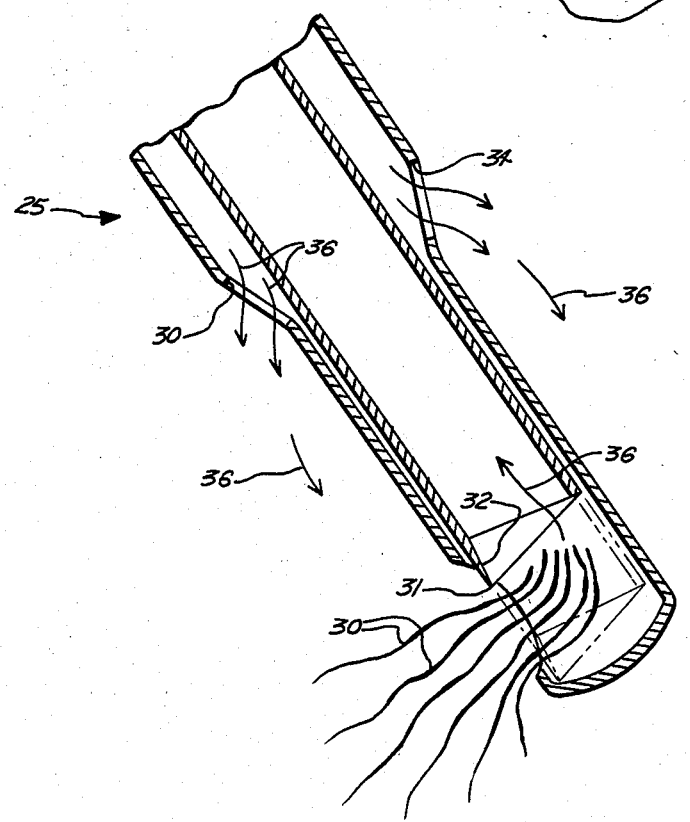
FIG. 2 is a sectional view of the tip of a microsurgical instrument for performing vitreous surgery.

FIG. 1 illustrates an ocular globe or eye 12 which includes a lens 13, cornea 14, anterior chamber 15, iris 16, ciliary body 17, vitreous body 18, optic nerve 20, retina 21, sclera 22 and choroid 23. An instrument 25, the tip of which is shown in greater detail in FIG. 2, is a surgical needle 0.4 to 1.0 mm in outside diameter formed of stainless steel which is attached to a handpiece (not shown) for manipulation by the surgeon. The handpiece can be connected through a flexible plastic tube (not shown) either to a saline solution reservoir for irrigation (not shown) or a pumping system for aspiration (not shown). The details of elements not shown are known to those with ordinary skill in the art and need not be described in detail in order to practice the invention.

The instrument 25 is a known irrigation/aspiration/cutting tip and is shown in FIG. 1 as being inserted in the vitreous 18. Suction is used to aspirate diseased tissue 30 into a side opening 31 of the instrument 25. As shown best in FIG. 2, the tissue is cut by a curved microguillotine blade 32 which is actuated by the surgeon and slidable in the instrument 25. A saline solution or the like is discharged through outlets 33, 34, and infuses the operation site. The infusion, in combination with controlled suction through the opening 31, helps to draw the tissue fragments 30 into the instrument 25 for removal after they are cut by the blade 32. Arrows 36 in FIG. 2 illustrate both the discharge of saline solution and suction action mentioned above.

The conventional instrument shown in FIGS. 1 and 2, however, has no provisions for measuring in-situ the suction force used to draw the diseased tissue 30 into the instrument 25 prior to cutting. Since the tissue removed by the vitrectomy procedures is usually located in the immediate vicinity of the retina 21, the danger of inadvertent damage to the retina 21 or other healthy tissue by excessive suction force during vitrectomy is considerable.

The embodiment of the invention illustrated in FIGS. 3 and 5 solves this problem by enabling the suction force to be monitored constantly. An instrument similar to the one in FIGS. 1 and 2 has been modified to measure pressure differences between the external and internal forces of its cutting/aspiration tip. The modified instrument is referred to generally by reference numeral 60 and includes an outer elongated housing 61 which surrounds an inner concentric guillotine 70 which carries a cutting blade 62 that cooperates with an opening 66 for surgically removing tissue fragments as described above. An inner bore or channel 63 operates to convey fluids and/or tissue. Only the tip of such an instrument is shown in FIG. 3 and additional features such as the discharge outlets 33, 34, shown in FIG. 2 were omitted to simplify the description.

A pressure transducer 65 is mounted in a chamber 65a located near aspiration inlet 66, the chamber 65a being bounded by two parallel diaphragms 67, 68, formed of silicon rubber inserts that are about 1 mm in diameter. The diaphragms 67, 68, are connected to the instrument 60 by means of an epoxy resin. The transducer 65 is preferably mounted at the outer end 61(a) of the tip of the housing 61.

Pressure transducer 65 is preferably a cantilever beam, piezo-resistive element known to the art which is capable of measuring intraocular pressure with the required sensitivity ($\pm 1$ mm. Hg), stability and linearity. Other types of piezo-resistive transducers, as well as photo-electric sensors operating in conjunction with fiber-optic light guides which transmit signals in the form of variations in light intensity caused by pressure differences moving a reflective surface can also be used in conjunction with the invention without substantially altering the size, shape or function of the instrument. An electrical signal generated by the transducer 65 is carried through wire leads 71 to a monitor/console (not shown) which is known in the art and contains a suitable power supply as well as the necessary electrical circuits for conditioning, amplifying and displaying the pressure measurement.

The piezoelectric elements 65(b) are attached to a cantilever beam and a rigid beam 65c, which is anchored to the wall of the instrument. Wire leads 71 which carry electrical signals from the transducer 65, are connected to the exterior surface of the instrument 60 so as to avoid interference with the action of the guillotine cutter 70. The leads 71 are bonded to the instrument 60 so that they are part of its smooth outer surface.

The vitrectomy suction instrument 60 significantly enhances safety through sensitivity to suction force and consequently intraocular pressure during surgery. As the surgeon aspirates strands of diseased tissue into the opening 66, the local pressure difference measured between diaphragms 67, 68, by the transducer 65 results in a relative pressure reading that reflects the forces exerted on the tissue strands as they enter the aspiration inlet 66. These forces fluctuate continuously because of differences in the viscoelastic properties of the manipulated tissue and the viscosity of the surrounding vitreous. The force level at any given time can fall in a range that departs considerably from the average force and the pressure in the vacuum line can be adjusted to accommodate these fluctuating force levels. By using the transducer 65, a signal can be generated to activate momentarily a vacuum relief valve in a known way (not shown) when the local pressure exceeds preset levels to adjust the suction when the force level falls outside the permissible range. Thus, the instrument 60 operates to reduce considerably the danger of damage to healthy tissue by preventing excessive instantaneous peaks in local suction forces.

Referring to FIGS. 4 and 6, another embodiment of the invention is illustrated, this one being directed to a surgical instrument which can measure intraocular pressure while performing an irrigation or aspiration procedure. The instrument is generally designated by reference numeral 40 and is an elongated body 41 formed of surgical grade stainless steel with an outside diameter of approximately 1 mm. The body 41 is divided through substantially its entire length into two parallel channels 42, 43, that are separated by an internal wall 49. Channel 43 is an irrigation/aspiration channel which is connected through a handpiece (not shown) to either a saline supply reservoir (not shown) or a vacuum system (not shown). The channel 43 has an outlet 44 located near the apex 45 of the tip of the instrument 40.

A transducer 50 is mounted in the portion of the channel 42 adjacent to the tip of the instrument 41, the channel 42 being vented to the atmosphere at a suitable site away from the operating field. The transducer 50 is of the type described above for the embodiment of FIGS. 3 and 5 and is connected to the instrument 40 through a base 55a. At the tip of the instrument 40, the transducer channel 42 terminates at a window 46 which is located adjacent to the outlet 44. The window 46 is approximately 1 mm in diameter and is fitted with a diaphragm 47 formed of silicon rubber. The diaphragm 47 is connected to the window 46 by means of epoxy resin. Wire leads designated by reference numeral 52 carry electrical signals generated by the transducer 50 to suitable instrumentation (not shown) for translating the signals into useful information for monitoring and regulating intraocular pressure.

The intraocular pressure probe 40 is suitable for the measurement and control of intraocular pressure during closed system procedures in the anterior chamber 15 as well as in the vitreous chamber 18. The instrument 40 can be inserted at a site separate from the operating incision and remain in place throughout the entire procedure, providing to the surgeon an independent source of determining and/or controlling intraocular pressure for providing information used in tamponade, suture tension controls and final approximation of physiologic pressure at the end of wound closure.

The invention which is embodied in the instruments described above is useful in constantly monitoring both intraocular fluid pressure and suction forces during ophthalmic surgery. By allowing the surgeon the benefit of this type of information, much of the guesswork is removed, resulting in safer and more accurate surgical procedures.

Although different embodiments of the invention may vary in detail they are still intended to be within the scope of the inventive concept described above. The details described in the foregoing preferred embodiment are intended to be illustrative and not limiting in any sense.

What is claimed as the present invention is:

1. An ophthalmic device for measuring relative pressure of fluid inside an ocular globe, the device being of the type adapted to cooperate with a fluid transfer means which is located external of the ocular globe and capable of supplying or removing intraocular fluid in response to predetermined signals, the device comprising:
   (a) an elongated surgical instrument adapted to penetrate the ocular globe;

(b) pressure sensitive means mounted on the instrument for moving in response to relative pressure changes in intraocular fluid;

(c) transducer means communicating with the pressure sensitive means for generating signals in response to movement of the pressure sensitive means;

(d) signal means for transmitting signals to the fluid transfer means; and (e) first conduit means operatively connected between the fluid transfer means and the interior of the ocular globe so that fluid can be supplied to or removed from the ocular globe in response to said signals.

2. The device of claim 1, wherein the the conduit means is formed in the instrument with an opening for communicating with the intraocular fluid.

3. The device of claim 2, wherein the pressure sensitive means includes a flexible diaphragm, and the signal means includes a pressure transducer in physical contact with the diaphragm for generating an electrical signal in response to movement of the diaphragm caused by pressure differences in the intraocular fluid.

4. The device of claim 3, wherein the diaphragm is located on the outer surface of the instrument and the instrument includes a second conduit in which the transducer is mounted, the second conduit communicating with the atmosphere so that the transducer can determine intraocular fluid pressure changes relative to atmospheric pressure.

5. The instrument of claim 4, wherein the instrument includes an outer end and the portion of the second conduit in which the transducer is located is formed in the outer end of the instrument and the chamber extends along the instrument parallel to the first conduit means.

6. The device of claim 3, wherein the instrument further includes a second conduit communicating with the interior of the ocular globe and adapted for connection to a suction means, cutting means associated with the second conduit for performing surgical operations within the ocular globe, and a chamber having at least a portion located between the intraocular fluid and second conduit and being separated from the fluid and second conduit by first and second diaphragms respectively, the pressure transducer contacting both diaphragms for generating a signal in response to relative pressure changes between fluid in the ocular globe and the second conduit.

7. The device of claim 6, wherein the first and second diaphragms are parallel and the first diaphragm is located on the outer end of the instrument.

8. The device of claim 6, wherein the first and second conduits are concentric, the first conduit terminating short of the portion of the second conduit that communicates with the intraocular fluid.

9. The instrument of claim 1, wherein the transducer means includes a cantilevered piezo-resistive element mounted on the instrument in physical contact with the pressure sensitive means.

10. A system for measuring fluid pressure inside an ocular globe and maintaining a predetermined fluid pressure therein, comprising:

(a) an elongated surgical instrument adapted to penetrate the ocular globe;

(b) fluid pressure transducer means mounted on the instrument on a position to communicate with fluid inside the ocular globe and generate signals in response to pressure changes in said fluid;

(c) means for transmitting the signals external of the instrument;

(d) fluid transfer means operatively connected to the transducer means for receiving said signals and supplying or removing fluid from the ocular globe in response to predetermined signals; and (e) a conduit operatively connected to the fluid transfer means and adapted to communicate with the interior of the ocular globe through which fluid can flow between the fluid transfer means and the ocular globe.

11. The system of claim 10, wherein the fluid pressure transducer means includes a flexible diaphragm, and a pressure transducer in physical contact with the diaphragm for generating an electrical signal of pressure information in response to movement of the diaphragm caused by pressure changes in the intraocular fluid.

12. The system of claim 10, wherein the fluid pressure transducer means is mounted on the portion of the instrument adapted to penetrate the ocular globe.

13. The system of claim 10, wherein the conduit is formed within a second elongated surgical instrument adapted to penetrate the ocular globe.

14. The system of claim 10, wherein the conduit is formed within said elongated surgical instrument.

15. The system of claim 10, wherein the pressure sensitive means includes a flexible diaphragm in a position to contact intraocular fluid when the instrument has penetrated the ocular globe, and the means for transmitting signals includes a pressure transducer in physical contact with the diaphragm for generating an electrical signal in response to movement of the diaphragm caused by pressure differences in the intraocular fluid.

16. The system of claim 15, wherein the diaphragm is located on the outer surface of the instrument and the instrument includes a second conduit in which the transducer is mounted, the second conduit communicating with the atmosphere so that the transducer can determine intraocular pressure changes relative to atmospheric pressure.

17. The system of claim 16, wherein the portion of the second conduit in which the transducer is located is formed in the end of the instrument and the second conduit extends along the instrument parallel to the first conduit.

18. The system of claim 10, wherein the transducer means includes a cantilevered piezo-resistive element mounted in the chamber in physical contact with the pressure sensitive means.

* * * * *